United States Patent
Ball et al.

(10) Patent No.: US 6,863,690 B2
(45) Date of Patent: Mar. 8, 2005

(54) HUMERAL SHOULDER PROSTHESIS

(75) Inventors: Robert J. Ball, Winona Lake, IN (US); Jeffrey M. Ondrla, Leesburg, IN (US); Laurent LaFosse, Annecy LeViuex (FR); Anne-Céline Godest, Lyons (FR)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 10/256,477

(22) Filed: Sep. 27, 2002

(65) Prior Publication Data

US 2004/0064187 A1 Apr. 1, 2004

(51) Int. Cl.⁷ .................................................. A61F 2/40
(52) U.S. Cl. .................................................. 623/19.11
(58) Field of Search .......................... 623/11.11, 19.11, 623/19.12, 19.13, 19.14, 18.11, 22.11, 22.4, 22.41, 22.42, 22.43, 22.44, 22.45, 22.46, 23.11, 23.12, 23.15

(56) References Cited

U.S. PATENT DOCUMENTS

| | | | |
|---|---|---|---|
| 4,908,032 A | | 3/1990 | Keller |
| 4,938,773 A | | 7/1990 | Strand |
| 5,002,578 A | | 3/1991 | Luman |
| 5,197,989 A | * | 3/1993 | Hinckfuss et al. ........ 623/22.42 |
| 5,314,479 A | * | 5/1994 | Rockwood et al. ...... 623/19.14 |
| 5,358,526 A | | 10/1994 | Tornier |
| 5,456,686 A | * | 10/1995 | Klapper et al. ............... 606/99 |
| 5,489,309 A | * | 2/1996 | Lackey et al. ............ 623/19.14 |
| 5,702,457 A | | 12/1997 | Walch et al. |
| 5,702,486 A | * | 12/1997 | Craig et al. ............... 623/19.14 |
| 5,723,018 A | * | 3/1998 | Cyprien et al. ........... 623/19.13 |
| 5,741,335 A | | 4/1998 | Gerber et al. |
| 5,858,020 A | | 1/1999 | Johnson et al. |
| 5,902,340 A | | 5/1999 | White et al. |
| 5,906,644 A | | 5/1999 | Powell |
| 6,102,953 A | | 8/2000 | Huebner |
| 6,206,925 B1 | | 3/2001 | Tornier |
| 6,217,615 B1 | * | 4/2001 | Sioshansi et al. ......... 623/18.11 |
| 6,228,120 B1 | | 5/2001 | Leonard et al. |
| 6,494,913 B1 | * | 12/2002 | Huebner ................... 623/19.11 |
| 6,530,957 B1 | * | 3/2003 | Jack ......................... 623/19.14 |
| 6,589,282 B2 | * | 7/2003 | Pearl ........................ 623/19.14 |
| 2001/0011193 A1 | | 8/2001 | Nogarin |
| 2002/0016634 A1 | * | 2/2002 | Maroney et al. ......... 623/19.14 |

FOREIGN PATENT DOCUMENTS

| | | | |
|---|---|---|---|
| EP | 0 712 617 | 5/1996 | |
| EP | 0898946 | 3/1999 | |
| EP | 1 043 001 | 10/2000 | |
| FR | 2579454 | 10/1986 | |
| FR | 2699400 | 6/1994 | |
| FR | 2699400 A1 * | 6/1994 | ............. A61F/2/40 |
| WO | WO 96/17553 | 6/1996 | |

\* cited by examiner

*Primary Examiner*—Todd E. Manahan
*Assistant Examiner*—Anuradha Ramana
(74) *Attorney, Agent, or Firm*—Maginot, Moore & Beck

(57) ABSTRACT

The humeral portion of a shoulder prosthesis includes a diaphyseal component configured for fixation within the humerus, a metaphyseal component, configured for removable implantation within the metaphysis of the humerus, and an engagement mechanism for removably engaging the two components. The metaphyseal component can initially include a convex articulating surface that can be replaced with a concave surface during the shoulder arthroplasty procedure or in a subsequent revision surgery. The metaphyseal component can also include a feature to facilitate removal of the component from the bone once it has been disengaged from the diaphyseal component.

9 Claims, 2 Drawing Sheets

HUMERAL SHOULDER PROSTHESIS

BACKGROUND OF THE INVENTION

The present invention relates generally to prosthetic joints, and more particularly to a shoulder prosthesis. The invention has specific application with respect to the humeral component of the shoulder prosthesis.

Conventional prostheses for the replacement of the shoulder joint include a segment engaged within the humerus bone and a mating articulating segment affiliated with the glenoid bone. In the typical shoulder prosthesis, the upper portion of the humerus is replaced by a unitary structure. This structure includes a stem designed to extend downwardly into bore or cavity formed within the humerus. This stem is secured within the bone by bone cement or through the use of coatings designed to promote ingrowth to secure the stem in place. Again with the conventional prosthesis, the stem is attached to a body portion that is designed to replace portions of the humerus at the anatomical neck of the bone. A generally spherical head portion projects from a surface of the body. This spherical head mates with a complementary concave articulating component mounted within the glenoid.

In recent years, modular shoulder prostheses have been developed to account for the different anatomies of the shoulder joint among patients. For instance, differently sized prostheses are necessary to accommodate the different bone sizes of prospective patients. Similarly, different shoulder joints require different angles of inclination of the articulating elements relative to the long axis of the humerus bone. Thus, a variety of modular prostheses have been developed that permit substitution of particular components of the prosthesis as necessary prior to implantation. One example of such a shoulder prosthesis system is disclosed in U.S. Pat. No. 5,314,479, owned by the assignee of the present invention, the disclosure of which is incorporated herein by reference.

One problem faced by both the conventional and the modular shoulder prosthesis is the deterioration of the shoulder joint that can accompany a shoulder arthroplasty. For instance, a patient who has undergone shoulder arthroplasty may experience loss of soft tissue strength, specifically at the rotator cuff, which can eventually lead to a total loss of key constraints that maintain the patency of the joint. This loss of soft tissue and soft tissue strength can allow unnatural joint loads to be produced, which can compromise the function of the prosthetic joint and/or lead to joint pain.

One solution for this problem for this problem is revision of the shoulder prosthesis. This revision can entail the substitution of different articulating components, or differently sized prosthetic components. In one treatment, the shoulder prosthesis is changed to a "reverse" type of prosthesis. A typical prosthetic shoulder replicates the standard anatomy of the joint. Specifically, the humeral component provides a convex articulating surface, much like the natural humeral end of the bone. This convex surface mates with a concave glenoid component.

A "reverse" type prosthesis essentially reverses the arrangement of the articulating surfaces. Specifically, the glenoid component includes a convex or partially spherical component, while the complementary concave surface is integrated into the humeral component. One consideration involved in the use of a reverse prosthesis is that the concave articular surface that is now part of the humeral component may actually protrude into the metaphyseal region of the humerus. This modified geometry can require modification of the metaphyseal portion of the humerus bone as well as the prosthesis.

Prior systems have required total revision of the joint. A total revision entails removal of the entire implant, including the stem that is fixed within the diaphyseal portion of the humerus. Of course, this surgical procedure is very difficult and invasive, and can place the patency of the patient's existing bone at risk. In view of these deleterious effects, what is needed is a shoulder prosthesis system that simplifies the revision process and that allows ready replacement of a standard joint component with a reverse-type component.

SUMMARY OF INVENTION

In order to address this need, the present invention contemplates a method for performing a revision of a shoulder arthroplasty comprising the initial step of implanting a shoulder arthroplasty including a diaphyseal component fixed within the diaphysis of the humerus bone, and a metaphyseal component implanted within the metaphysis of the humerus bone. The metaphyseal component is removably engaged to the diaphyseal component which carries a first articulating element. In order to perform the revision, the metaphyseal component is disengaged from the diaphyseal component while maintaining the diaphyseal component fixed within the humerus bone.

The metaphyseal component having a first articulating element is then removed and a metaphyseal component having a second articulating element is provided. This new metaphyseal component having the second articulating element is then engaged to the diaphyseal component, all while the diaphyseal component is fixed within the humerus bone. In accordance with one aspect of the invention, one of the first and second articulating elements includes a convex articulating surface, while the other of the articulating elements is a concave articulating surface.

In a typical instance, the initial metaphyseal component will have the standard convex, or spherical ball element. The revision procedure would then be conducted to replace the humeral component with a concave element. Thus the method further comprises the step of revising the glenoid component of the shoulder arthroplasty for articulating engagement with the second articulating element.

While one aspect of the invention contemplates improvements to a revision procedure, certain features of the invention can be implemented intraoperatively during the initial arthroplasty procedure. For instance, when the humeral components of the shoulder prosthesis are implanted, a decision can be made as to which type of articular element should be employed. Initially, the standard convex humeral element can be provided. If further evaluation reveals that a reverse-type component would be better suited for the prosthesis, the metaphyseal component can be replaced without disturbing the diaphyseal component already fixed within the humerus.

In a preferred embodiment of the procedure, the first and second articulating elements are different—i.e., conventional convex versus reverse-type concave. However, the two elements can be similarly configured, but having different dimensions or geometries. For instance, the invention further contemplates replacing a metaphyseal component having a ball element of a certain diameter with a new metaphyseal component having a ball element of a larger or smaller diameter. Likewise, the anteversion/retroversion between the metaphyseal component and the diaphyseal component can be altered from the anteversion/retroversion prior to the removal step.

In one embodiment of the invention, an entirely new metaphyseal component is substituted for the initial removed component. In an alternative embodiment, the body of the original metaphyseal component is retained and only the articulating element is replaced.

In another aspect of the invention, a humeral shoulder prosthesis is provided comprising a diaphyseal component configured for fixation within a bore defined in the diaphysis of the humerus bone. The diaphyseal component defines a longitudinal axis that is substantially coincident with the axis of the humerus bone when the component is fixed therein. The prosthesis further includes a metaphyseal component configured for implantation within a bore defined in the metaphysis of the humerus bone. The metaphyseal component has an outer surface configured for removal from the bore in the metaphysis, meaning that outer geometry of the component does not create the need for removal of bone in order to extract the component from the metaphysis of the bone.

An articulating element is associated with metaphyseal component that has an articulating surface for engaging a complementary configured surface associated with the glenoid bone. The articulating surface can be concave, convex or some other configuration suited for a shoulder arthroplasty. In one aspect of the invention, an engagement mechanism is provided that extends generally along the longitudinal axis of the diaphyseal component and that is operable to engage the metaphyseal component to the diaphyseal component. The engagement mechanism is configured to permit ready disengagement of the metaphyseal component from the diaphyseal component when the diaphyseal component is fixed within the humerus bone.

In certain embodiments of the invention, the diaphyseal component includes a proximal surface defining a first bore therein. The bore includes a threaded portion, while the engagement mechanism includes a screw having threads configured to threadedly engage the threaded portion of the first bore. The metaphyseal component includes a proximal surface and an opposite distal surface configured to contact the proximal surface of the diaphyseal component. The metaphyseal component further defining a second bore extending from the proximal surface to the distal surface. The screw of the engagement mechanism then includes a head configured for engagement within the second bore. The screw can thus be extended through the second bore in the metaphyseal component to engage the threaded bore in the diaphyseal component. Tightening the screw threads clamps the two components together. Preferably, the second bore defines a countersunk portion sized to engage the head of the screw below the proximal surface.

In a further feature, the second bore can include a threaded portion apart from the engagement mechanism. This second threaded portion can be disposed between the countersunk portion and the distal surface of the metaphyseal component. In one embodiment, the second threaded portion is configured to prevent engagement by the threads of the screw of the engagement mechanism. Instead, the second threads can be configured to engage the threaded end of a removal/insertion tool. The tool can essentially include a threaded shaft having a handle for manual engagement. When it is desired to remove the metaphyseal component, the screw of the engagement mechanism is removed from both the diaphyseal and metaphyseal components, and the tool is engaged to the metaphyseal component.

The engagement mechanism can further include a press-fit feature between the distal surface of the metaphyseal component and the proximal surface of the diaphyseal component. In one aspect of the invention, this press-fit feature can include a tapered boss extending from the distal surface of the metaphyseal component and a tapered portion of the first bore at the proximal surface of the diaphyseal component.

In certain embodiments, the metaphyseal component includes an angled surface relative to the longitudinal axis, the angled surface associated with the articulating element. The articulating element can include a concave surface defined in the angled surface, the concave surface configured for complementary engagement with a convex surface associated with the glenoid bone.

Alternatively, the angled surface of one metaphyseal component can define a mounting bore, and the articulating element can include a convex humeral head and a mounting feature configured for engagement within the mounting bore. In selected embodiments, the articulating element can incorporate a concave surface with a mounting feature configured for engagement within the mounting bore.

It is one object of the invention to provide a humeral prosthesis for a shoulder arthroplasty. A further object resides in method steps fro performing a revision procedure without disturbing a diaphyseal component fixed within the humerus.

One significant benefit of the present invention is that it permits a revision procedure that minimizes the invasiveness of the procedure. Another benefit of the invention is that it allows intraoperative selection of standard or reverse components for the humeral prosthesis of a shoulder arthroplasty. Other benefits and objects of the invention can be readily discerned from the following written description taken together with the accompanying figures.

DESCRIPTION OF THE PREFERRED EMBODIMENTS

Figure 1:
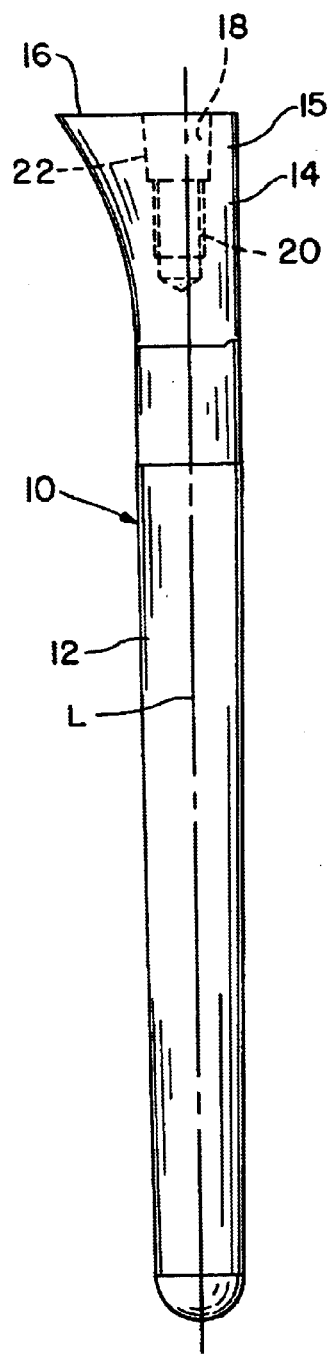
FIG. 1 is a side elevational view of a diaphyseal component of a shoulder prosthesis in accordance with one embodiment of the present invention.

For the purposes of promoting an understanding of the principles of the invention, references will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the inventions as would normally occur to one skilled in the art to which this invention pertains.

The present invention contemplates a shoulder prosthesis, and most particularly the humeral segment of the shoulder prosthesis. In accordance with the present invention, the humeral segment includes three components, a diaphyseal component, a metaphyseal component, and a fixation element. The diaphyseal component is configured for engagement within a prepared bore in the diaphysis of the humerus bone. The metaphyseal component is configured for removable implantation within the metaphyseal portion of the humerus bone. The humeral articulating element of the shoulder prosthesis is associated with the metaphyseal component. In accordance with certain features of the invention, this articulating element can be of conventional design including a convex or semi-spherical surface. On the other hand, the present invention contemplates an articulating element that is concave to receive a convex surface associated with the glenoid.

In order to accomplish these features of invention, the shoulder prosthesis includes a diaphyseal component 10, shown in FIG. 1. The component includes an elongated stem 12 that defines a longitudinal axis L. The stem 12 is configured for implantation within a prepared bore along the diaphysis of the humerus bone. The stem 12 can be sized and configured similar to prior humeral implants. The stem can be fixed within the humerus by way of bone cement, or by way of some form of bone engaging or bone growth inducing surface treatment to the stem 12.

The proximal end of the stem terminates in a shoulder 14. This shoulder includes a flared portion 15 that emulates the transition to the metaphyseal portion of the humerus. The shoulder 14 defines a proximal surface 16 that eventually faces the glenoid when the diaphyseal component 10 is implanted within the humerus. A bore 18 extends from the proximal surface 16 of the diaphyseal component 10. Preferably, the bore 18 extends along a substantial portion of the length of the shoulder 14. In addition, the bore 18 is preferably aligned parallel to and closely adjacent the longitudinal axis L of the stem 12. Likewise, the proximal surface 15, and more specifically the centroid of the surface, is also preferably offset from the longitudinal axis L.

As can be seen in FIG. 1, the bore 18 includes a threaded portion 20 adjacent the blind end of the bore. The bore also defines a tapered portion 22 between the proximal surface 16 and the beginning of the threaded portion 20. Preferably, the tapered portion 22 is formed at a Morse taper angle. The threads in the portion 20 can be formed as standard machine threads. However, it is preferable that the threaded portion 20 be finely threaded to enhance the fixation effect achieved by the engagement screw described below.

Figure 2:
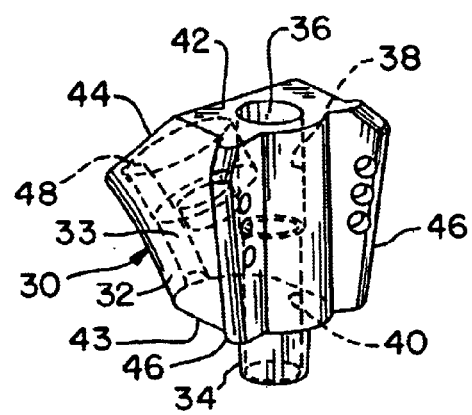
FIG. 2 is a perspective view of a metaphyseal component of a shoulder prosthesis in accordance with one embodiment of the present invention, suited for engagement with the diaphyseal component depicted in FIG. 1.
Figure 3:
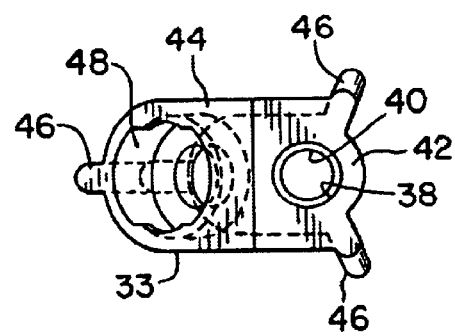
FIG. 3 is a top elevational view of the metaphyseal component shown in FIG. 2
Figure 4:
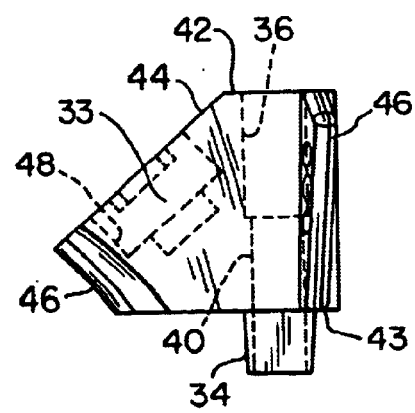
FIG. 4 is a side elevational view of the metaphyseal component shown in FIGS. 2 and 3.

The shoulder prosthesis further includes a metaphyseal component 30, which is depicted in FIGS. 2–4. The metaphyseal component 30 is formed by a body 32 that is sized and shaped for implantation within the metaphyseal region of the humerus. More particularly, the outer surface 33 of the body 32 is formed so that the metaphyseal component 30 can be readily removed from the humerus bone during a revision surgery or during initial shoulder arthroplasty procedure. Thus, as can be appreciated upon consideration of FIGS. 2–4, the outer surface defines substantially parallel or outwardly diverging surface portions that did not physically anchor within the proximal portion of the humerus.

The present invention contemplates an engagement mechanism that is operable to engage the metaphyseal component to the diaphyseal component. This engagement mechanism includes the bore 18 in the diaphyseal component 10, and also includes a press-fit boss 34 projecting from the distal surface 43 of the component 30. The distal surface 43 is sized and shaped for contact engagement with the proximal surface 16 of the diaphyseal component 10. The profile of the distal surface 43 preferably emulates the profile of the proximal surface 16. The boss 34 projects downwardly, or distally, from the distal surface 33, and is sized and configured for a press-fit engagement within the tapered portion 22 of the bore 18 of the diaphyseal component. Again, as with tapered portion 22, the press-fit bore 34 is preferably defined at a Morse taper angle to generate an optimum press-fit.

Another element of the engagement mechanism contemplates a through bore 36 that is defined between the proximal surface 42 and the distal surface 43 of the metaphyseal component. This through bore 36, along with the boss 34, are co-linear with the bore 18. Thus, the elements of the engagement mechanism can extend generally parallel with the longitudinal axis L of the stem 12 of the diaphyseal component. In other embodiments, the through bore 36 and bore 18 may not be parallel to the axis L, depending upon the overall configuration of the metaphyseal component 14. However, it is important that the opening of the through bore be accessible in situ to allow use of a driving tool extending into the bores.

In accordance with certain features of the present invention, the through bore 36 includes two portions. A first counter-sunk portion 38 is immediately adjacent the proximal surface 42. The bore further defines a threaded portion 40 between the counter-sunk portion 38 and the distal surface 43. The bore continues through the press-fit boss 34, but is preferably not threaded or counter-sunk. These aspects of the through bore 36 and its particular function will be described below.

The metaphyseal component 30 can include fixation fins 46 projecting from the outer surface 33. Again, keeping with the configuration of the outer surface 33, the fins are configured to permit ready removal of the metaphyseal component 30 from the proximal end of the humerus.

In a further aspect of the metaphyseal component 30, the body 32 defines an angled surface 44. This angled surface is associated with the articulating element of the humeral shoulder prosthesis and is preferably oriented at known angles for the articulating elements relative to the longitudinal axis L of the humerus. In the embodiment shown in FIGS. 2–4, this articulating element can include mounting features 48 defined in the angled surface 44. These mounting features are configured for mounting or engaging a humeral head prosthesis, such as the prosthesis 60 shown in FIG. 6. It is understood that the mounting feature 48 can be modified depending on the mounting features of the particularly selected humeral head prosthesis. Thus, the present invention contemplates a metaphyseal component 30 that can provide a variety of mounting features 48 to accommodate a variety of humeral head prostheses.

Figure 5:
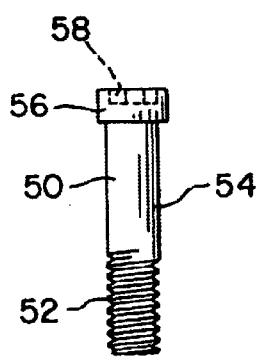
FIG. 5 is a side elevational view of a fixation screw used for connecting the metaphyseal and diaphyseal components illustrated in FIGS. 1–4.

The third component of the shoulder prosthesis of the present invention is illustrated in FIG. 5. Specifically, the component is an engagement screw 50 that includes a threaded shank 52 configured for threaded engagement with the threaded portion 20 of the diaphyseal component 10. The engagement screw 50 can include an unthreaded shank 54 between the threaded shank 52 and the head 56 of the screw. The head can define a driving feature 58, such as a hex recess, which is configured for engagement by a driving tool. The length of the threaded shank 52 is preferably calibrated to correspond to the length of the threaded portion 20. Similarly, the length of the unthreaded shank 54 can be calibrated to be slightly less than the distance from the base of the counter-sunk portion 38 to the proximal surface 16 of the diaphyseal component 10. More specifically, the length of the threaded and unthreaded shanks can be calibrated so that the engagement screw 50 can be fully and tightly engaged within the threaded portion 20 so the head 56 presses against the counter-sunk portion 38 of the metaphyseal component 30. Of course, it should be understood that the purpose of the engagement screw 50 is to connect or engage the metaphyseal component 30 to the diaphyseal component 10.

Figure 6:
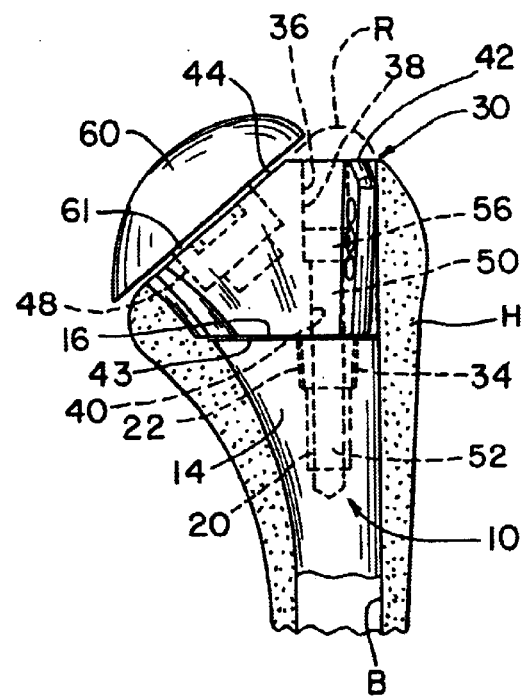
FIG. 6 is a side partial cut-away view of a humerus bone with the components of the shoulder prosthesis of the present invention mounted therein.

Referring now to FIG. 6, the implantation of the components of the shoulder prosthesis of the present invention can be understood. The humerus H is prepared by creating a cavity or bore B through the diaphysis of the bone in a conventional manner. The head of the humerus H is also prepared in a known manner, particularly by removing the humeral head. In addition to the normal resection across the humeral head, an additional segment of the humerus H, shown in the phantom line designated R, is resected. Removal of this additional bone material allows for direct insertion of the diaphyseal component 10 along the longitudinal axis of the humerus H. The diaphyseal component 10 is implanted within the bore B in the humerus H in a known manner. For instance, bone cement can be injected into the bore for a firm fixation of the component 10 to the humerus H. Alternatively, if the stem 12 of diaphyseal component 10 includes a bone growth inducing surface treatment, bone cement may not be necessary. The diaphyseal component 10 is inserted into the bore B until the shoulder 14 rests at the base of the metaphysis of the humerus.

In the next step, the metaphyseal component 13 is implanted within the metaphysis of the humerus. As the metaphyseal component 30 is introduced into the top of the humerus H, the boss 34 extends into the tapered portion 22 of the bore 18 of the diaphyseal component 10. The metaphyseal component 30 is pushed toward the diaphyseal component 10 until the distal surface 43 contacts the proximal surface 16. At this point, the press-fit between the boss 34 and the tapered portion 22 should be complete and solid. Again, as described above, the two press-fit elements can be formed at a Morse taper angle for optimum fixation. As shown in FIG. 6, the amount of bone material removed from the humerus H is preferably measured to correspond to the outer profile of the metaphyseal component 30.

Thus, the proximal surface 42 and angled surface 44 are generally coextensive with the end of the prepared bore within the humerus H. With this configuration of the metaphyseal component 30 the through bore 36 is prominent and easily accessible at the prepared end of the humerus H. Thus, the bore 36 is easily accessed for introducing the engagement screw 50 to complete the engagement of the metaphyseal component 30 to the diaphyseal component 10. The engagement screw 50 can be introduced into the bore 36 and the threaded shank 52 is threaded into the threaded portion 20 of the diaphyseal component 10 using a conventional driving tool.

Preferably, the portion of the through bore 36 beneath the counter-sunk portion 38, which includes threaded portion 40, has a diameter that is greater than the outer diameter of the threaded shank 52. In this way, the threaded shank 52 can pass through the bore unimpeded for engagement with the threaded portion 20 in the diaphyseal component. The tightening of the engagement screw 50 within the threaded portion 20 of the bore of the diaphyseal component 10 will complete the engagement between the two components 30 and 10. Driving the screw into the threaded portion will also tighten the press-fit between the boss 34 and the tapered portion 22 and draw the distal surface 43 and the proximal surface 16 into solid contact.

Once the metaphyseal component 30 has been solidly engaged to the diaphyseal component 10, a humeral head prosthesis 60 can be connected to the metaphyseal component. In the illustrated embodiment, the humeral head prosthesis 60 includes a mounting feature 61 that is configured to mate with the mounting feature 48 of the metaphyseal component 30. For instance, the two mounting features can constitute a press-fit arrangement. Other mounting arrangements are contemplated, such as a threaded engagement, a collet-based engagement, variable angle connection, and any other connection mechanism known in the art. Once the humeral head prosthesis 60 has been attached to the metaphyseal component 30, the humeral shoulder prosthesis is ready to engage the glenoid component of the over-all shoulder assembly.

In the embodiment illustrated in FIG. 6, the metaphyseal component 30 comports with the standard configuration of shoulder prosthesis—namely the humeral head prosthesis 60 provides a convex or semi-spherical surface for engaging a corresponding concave surface in the glenoid. However, as explained above, certain difficulties arising from the shoulder arthroplasty may require revision. More specifically, it may be necessary to replace the humeral head prosthesis with a concave surface to mate with a convex/semi-spherical surface associated with the glenoid. In this circumstance, it is necessary to remove both the humeral head prosthesis 60 and the metaphyseal component 30.

In accordance with one embodiment of the invention, a revision surgical procedure is contemplated in which the humeral head 60 is first removed from the metaphyseal component 30. The engagement screw 50 is unthreaded from the threaded portion 20 of the diaphyseal component 10. In the preferred embodiment, the engagement screw 50 is completely removed from the assembly, but can be retained for reuse to connect a new metaphyseal component to the diaphyseal component 10. With this revision procedure, the diaphyseal component 10 remains implanted with the humerus H. Thus, the metaphyseal component 30 is disengaged from the diaphyseal component 10 while the latter component is still fixed within the bone.

Figure 7:
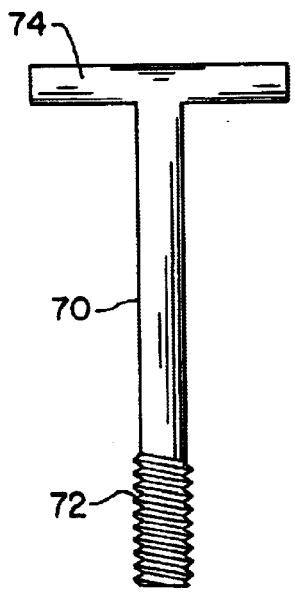
FIG. 7 is a side elevational view of a removal tool used to remove the metaphyseal component, such as during a revision surgery.

In order to remove the metaphyseal component 30, a removal tool, such as the tool 70 shown in FIG. 7, can be provided. The removal tool 70 can include a threaded end 72 that is configured to engage the threads 40 within the through bore 36 of the metaphyseal component 30. The tool can also be provided with a handle 74 or some other comparable manual gripping feature. In accordance with the inventive revision procedure, the removal tool 70 can be engaged within the threaded portion 40 of the through bore 36. The tool 70 is then used to dislodge the press-fit boss 34 of the metaphyseal component 30 from the tapered portion 22 of the bore 18 in the diaphyseal component 10. If bone cement has been used to help fix the metaphyseal component 30, the cement is preferably loosened using some conventional means to facilitate removal of the component 30.

As one alternative to the removal tool 70, the threaded portion 40 of the through bore 36 can have threads that mate with the threaded shank 52 of the engagement screw 50. With this approach, the engagement screw can be unthreaded from the bore 18 of the diaphyseal component 10 and then threaded into the threaded portion 40 of the metaphyseal component 30. The head 56 of the engagement screw 50 can be engaged by a manipulation instrument that is then used to manipulate and remove the metaphyseal component 30. However, this approach is not optimum because the threaded shank 52 of the engagement 50 must be threaded through the threaded portion 40 of the metaphyseal component 30 before it can be engaged within the threaded portion 20 of the diaphyseal component 10.

Figure 8:
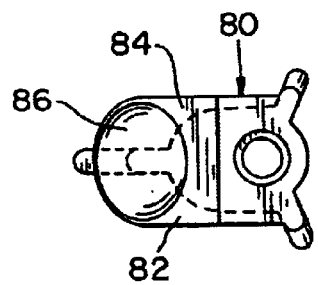
FIG. 8 is a top elevational view of an alternative embodiment of the metaphyseal component for use as a component of a shoulder prosthesis.
Figure 9:
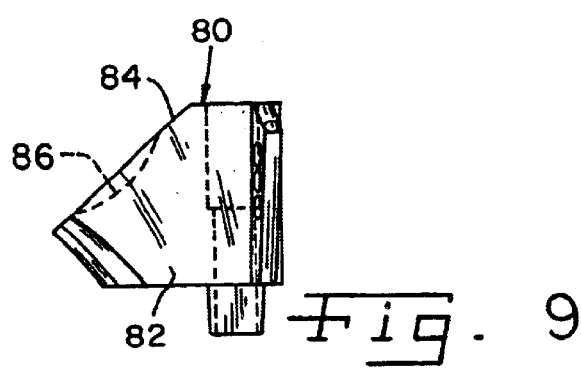
FIG. 9 is a side elevational view of the alternative metaphyseal component shown in FIG. 8.

Once the metaphyseal component has been removed a new metaphyseal component can be provided for implantation. Thus, as shown in FIGS. 8 and 9, a metaphyseal component 80 can be provided that includes a body 82 that can be configured substantially similar to the body 32 of the metaphyseal component 30. The principal difference between component 80 and component 30 is that the angled surface 84 defines a concave articulating surface 86. Thus, instead of providing a mounting feature, such as a mounting feature 48 of the metaphyseal component 30, the metaphyseal component 80 directly integrates the articulating surface 86 into the component itself. This reverse metaphyseal component 80 can be engaged to the implanted diaphyseal component 10 in the manner described above.

In the illustrated embodiment of FIGS. 8 and 9, the reverse metaphyseal component 80 is substantially similar in outer profile to the metaphyseal component 30. However, in some of the instances it may be contemplated that the reverse metaphyseal component 80 would have a different profile. In this case, special reamers can be used to reshape the proximal portion of the opening B in the humerus H. For example, where the concave articular surface 86 requires a particular depth or dimension, the angled surface 84 of the body 82 may be enlarged. This change would increase the overall profile of the reverse metaphyseal component 80 which could then require removal of additional bone of the proximal end of humerus H.

Once the reverse metaphyseal component has been implanted, the glenoid side of the shoulder prosthesis system can be prepared and a reverse component implanted that includes a convex articulating surface. It is contemplated that the reverse humeral and glenoid components would be provided as a matched set to ensure a proper articulating relationship between the two elements of the shoulder prosthesis.

In the above description, it has been presumed that the revision surgery occurs some time after the shoulder arthroplasty has been performed. However, the same substitution of metaphyseal components can occur during the initial arthroplasty procedure. Thus, the surgeon can intraoperatively select the use of a reverse component if the soft tissue stability is not sufficient to support a typical primary prosthesis. Whether the substitution occurs during the initial arthroplasty, or during a later revision, the procedure does not compromise the fixation of the diaphyseal component 10 within the humerus.

Again, while the preferred embodiments of the present invention contemplate changing metaphyseal components between a typical primary arrangement and reverse arrangement, substitution of the metaphyseal component can be for sizing considerations. For instance, once the bore B has been prepared within the humerus and the diaphyseal component 10 implanted, it may be determined that the distance between the proximal surface 16 of the diaphyseal component 10 and the proximal face of the prepared end of the humerus H will accommodate a bigger or smaller metaphyseal component. In that case, a different metaphyseal component having a greater or a lesser height from its proximal surface 42 to its distal surface 43 can be selected. Similarly, different metaphyseal components can be provided with different angular orientations of the angled surface, such as surfaces 44 on the component 30 or 84 on the component 80. In addition to sizing considerations, angular adjustments between the diaphyseal and metaphyseal components can be made intraoperatively. Thus, anteversion or retroversion can be adjusted through rotation of the metaphyseal component 30 about the diaphyseal component 10 prior to final engagement of the two components.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

For instance, the illustrated embodiments contemplate integrating the concave articulating surface 86 into the metaphyseal component 80. Alternatively, the metaphyseal component can be configured to support a further component carrying the concave bearing surface. Thus, in some embodiments, the replacement metaphyseal component can include means for attaching a polyethylene liner to the component, where the liner is concave for articulating contact with a metallic glenoid component.

What is claimed is:

1. A method for performing a revision of a shoulder arthroplasty comprising the steps of:
   implanting a shoulder prosthesis including a diaphyseal component fixed within the diaphysis of the humerus bone, and a metaphyseal component implanted within the metaphysis of the humerus bone and removably engaged to the diaphyseal component, having metaphyseal component having a first articulating element;
   disengaging the metaphyseal component from the diaphyseal component while maintaining the diaphyseal component fixed within the humerus bone;
   removing the metaphyseal component having a first articulating element;
   providing a metaphyseal component having a second articulating element; and
   engaging the metaphyseal component having a second articulating element to the diaphyseal component while the diaphyseal component is fixed within the humerus bone;
   wherein one of the first and second articulating elements includes a convex articulating surface, and the other of the articulating elements is a concave articulating surface.

2. The method for performing a revision of a shoulder arthroplasty according to claim 1, wherein:
   the first actuating element is removably engaged to the metaphyseal component;
   the step of disengaging the metaphyseal component includes disengaging second articulating element from the metaphyseal component; and
   the step of engaging the diaphyseal component includes engaging the second articulating element to the diaphyseal component.

3. The method for performing a revision of a shoulder arthroplasty according to claim 1, wherein the step of disengaging the metaphyseal component includes loosening bone cement between the metaphyseal component and the humerus bone.

4. A surgical procedure comprising the steps of:

implanting a shoulder prosthesis within a humerus bone so that (i) a distal component of the shoulder prosthesis is fixed within a first portion of the humerus, and (ii) a first proximal component of the shoulder prosthesis is fixed within a second portion of the humerus, said first proximal component being removably engaged to said distal component, and further said first proximal component including a first articulating element;

disengaging the first proximal component from the distal component while maintaining the distal component fixed within the first portion of the humerus bone;

removing the first proximal component having the first articulating element from the second portion of the humerus bone; and implanting a second proximal component having a second articulating element within the second portion of the humerus bone including engaging the second proximal component to the distal component while the distal component is fixed within the first portion of the humerus bone;

wherein one of the first and second articulating elements includes a convex articulating surface; and wherein the other of the first and second articulating elements includes a concave articulating surface.

5. The method of claim 4, wherein:

the first portion of the humerus bone includes the diaphysis of the humerus bone, and the second portion of the humerus bone includes the metaphysis of the humerus bone.

6. The method of claim 4, wherein:

the first articulating element includes a head component coupled to a first body of the first proximal component, and the second articulating element includes a concave bearing surface defined in a second body of the second proximal component.

7. The method of claim 6, wherein said head component is removably coupled to the first body of the first proximal component.

8. The method of claim 4, wherein said first articulating member is configured to mate with a bearing surface of a glenoid.

9. The method of claim 4, wherein the first proximal component removing step includes loosening bone cement between the first proximal component and the second portion of the humerus bone.

* * * * *